(12) United States Patent
Chen

(10) Patent No.: US 10,610,324 B2
(45) Date of Patent: Apr. 7, 2020

(54) STEREOTACTIC DEVICE

(71) Applicant: Chao-Hsien Chen, Chiayi (TW)

(72) Inventor: Chao-Hsien Chen, Chiayi (TW)

( * ) Notice: Subject to any disclaimer, the term of this patent is extended or adjusted under 35 U.S.C. 154(b) by 316 days.

(21) Appl. No.: 15/620,237

(22) Filed: Jun. 12, 2017

(65) Prior Publication Data

US 2018/0235720 A1    Aug. 23, 2018

(30) Foreign Application Priority Data

Feb. 17, 2017 (TW) .............................. 106105292 A

(51) Int. Cl.
*A61B 17/06*    (2006.01)
*A61B 90/11*    (2016.01)
*A61B 90/14*    (2016.01)
*A61B 90/10*    (2016.01)

(52) U.S. Cl.
CPC ............... *A61B 90/11* (2016.02); *A61B 90/14* (2016.02); *A61B 2090/103* (2016.02); *A61B 2503/40* (2013.01); *A61B 2503/42* (2013.01)

(58) Field of Classification Search
CPC ..... A61B 90/11; A61B 90/14; A61B 17/3403; A61B 2017/22075; A61B 2017/22077
See application file for complete search history.

(56) References Cited

U.S. PATENT DOCUMENTS

| | | | | |
|---|---|---|---|---|
| 2003/0109825 | A1* | 6/2003 | Loser ................. | A61B 17/3403 604/131 |
| 2005/0234435 | A1* | 10/2005 | Layer ................. | A61B 17/3403 606/1 |
| 2010/0030184 | A1* | 2/2010 | Boulis ................ | A61B 17/0206 604/500 |

FOREIGN PATENT DOCUMENTS

| | | |
|---|---|---|
| CN | 201814661 U | 5/2011 |
| CN | 202113169 U | 1/2012 |
| CN | 202198646 U | 4/2012 |
| CN | 103210077 A | 7/2013 |
| CN | 204219048 U | 3/2015 |
| CN | 204468218 U | 7/2015 |
| CN | 205107912 U | 3/2016 |
| CN | 105492052 A | 4/2016 |
| CN | 105726207 A | 7/2016 |
| CN | 105877812 A | 8/2016 |
| TW | 200833294 A | 8/2008 |
| TW | 200944178 A | 11/2009 |
| WO | 01/37747 A1 | 5/2001 |

(Continued)

*Primary Examiner* — Katherine M Rodjom

(74) *Attorney, Agent, or Firm* — Li & Cai Intellectual Property (USA) Office

(57) ABSTRACT

A stereotactic device of the present disclosure includes a base seat, a first moving module, a second moving module, a supporting module, and an operating module. The first moving module is disposed on the base seat and moves along a first direction, and the second moving module is disposed on the first moving module and moves along a second direction substantially perpendicular to the first direction. The supporting module is disposed on the second moving module and includes a supporting unit, and a grip unit that is disposed on the supporting unit. The operating module is disposed on the supporting module and includes a support unit, a rotating unit that is disposed on the support unit, a driving unit that is disposed on the support unit and that is co-movable with the rotating unit, and a sliding unit that is co-movable with the driving unit.

12 Claims, 17 Drawing Sheets

(56) References Cited

FOREIGN PATENT DOCUMENTS

WO        2009/060394 A1    5/2009
WO        2015/040407 A1    3/2015

\* cited by examiner

STEREOTACTIC DEVICE

CROSS-REFERENCE TO RELATED APPLICATION

This application claims priority of Taiwanese Patent Application No. 106105292, filed on Feb. 17, 2017.

FIELD

The present disclosure relates to a stereotactic device, and more particularly to a stereotactic device that can be hand-guided by a user.

BACKGROUND

A conventional stereotactic device is capable of moving along the X-Y-Z coordinates in space. In operation, a user first moves an injection needle along the X-Y plane of axis to an appropriate position over the test subject, e.g., over the brain of a lab mouse, then adjusts the position of the injection needle along the Z axis so as to pierce downwards into the brain and inject a medicinal drug.

However, in the conventional stereotactic device, positional adjustments along the X-Y-Z directions are made by turning knobs or dials that respectively correspond to each direction. Therefore, a user's hands need to constantly move between different knob positions when adjusting the needle along each direction. This is inconvenient and counterintuitive in operation.

SUMMARY

The objective of the present disclosure is to describe a stereotactic device that can improve the drawbacks associated with the prior art.

Accordingly, a stereotactic device of the present disclosure includes a base seat, a first moving module, a second moving module, a supporting module, and an operating module. The first moving module is disposed on the base seat and moves along a first direction while the second moving module is disposed on the first moving module and moves along a second direction substantially perpendicular to the first direction. The supporting module is disposed on the second moving module and includes a supporting unit, and a grip unit that is disposed on the supporting unit. The supporting module moves with the grip unit along one of the first and second directions when a force is exerted along one of the first and second directions on the grip unit. The operating module is disposed on the supporting module and includes a support unit, a rotating unit that is disposed on the support unit, a driving unit that is disposed on the support unit and that is co-movable with the rotating unit, and a sliding unit that is co-movable with the driving unit.

BRIEF DESCRIPTION OF THE DRAWINGS

Other features and advantages of the present disclosure will become apparent in the following detailed description of the exemplary embodiments represented by the accompanying drawings, of which.

DETAILED DESCRIPTION

The aforementioned illustrations and following detailed description are exemplary for the purposes of further explaining the scope of the present disclosure. Other objectives and advantages related to the present disclosure will be illustrated in the following description and appended drawings. Furthermore, the directional terms such as "left", "right", "upper" or "lower" are used for the purposes of describing the drawings and shall not be deemed as limitations to the present disclosure.

It should be understood that, although terms such as "first" and "second" are used to describe the components of the present disclosure in the description below, the components are not limited by these terms. Instead, the use of these terms is merely for the purpose of distinguishing components from each other. On the other hand, the term "or" may indicate that any one of the listed items or all the possible combinations thereof are included.

Figure 1:
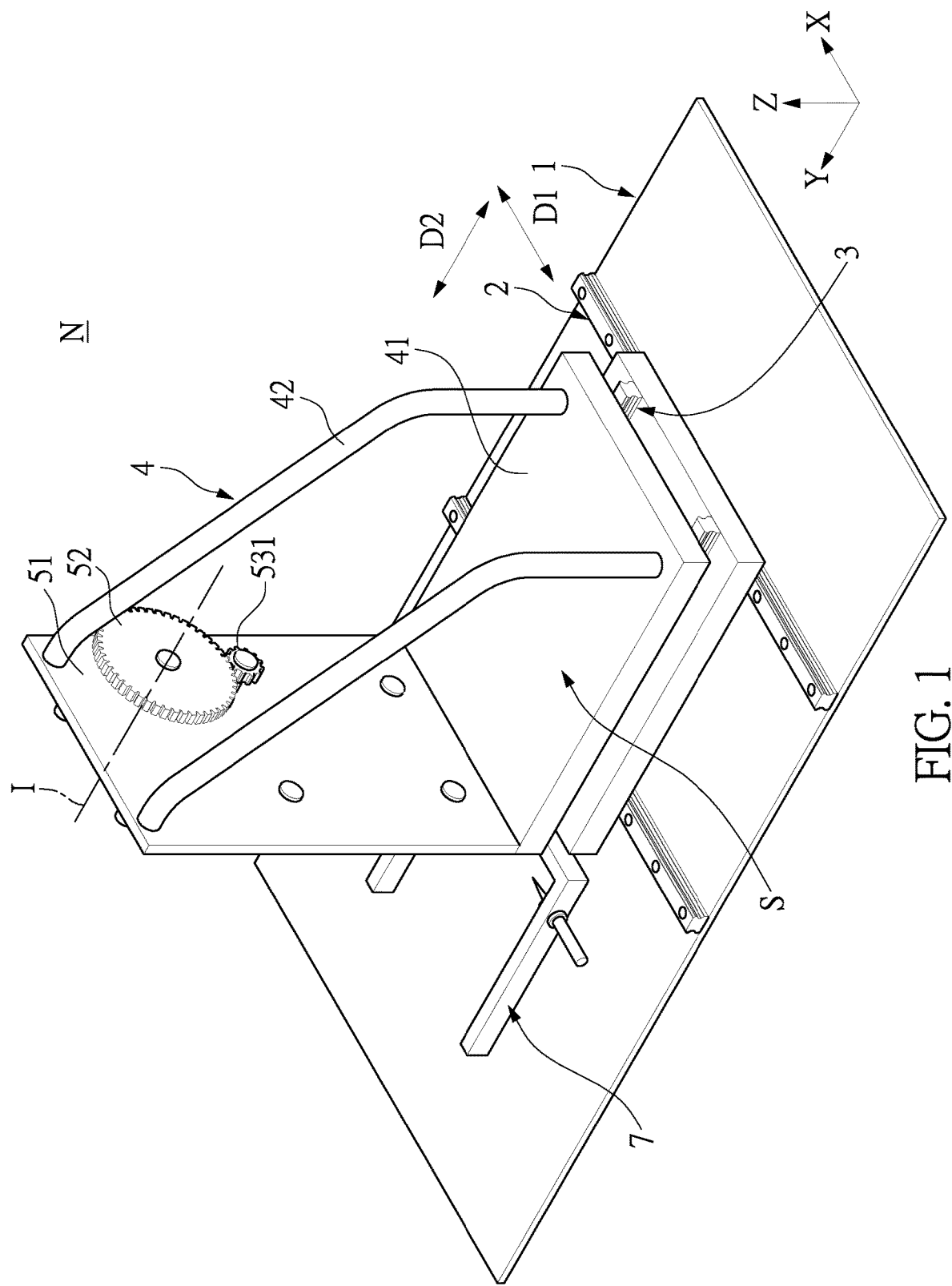
FIG. 1 is an assembled perspective view of a first embodiment of a stereotactic device according to the present disclosure.
Figure 2:
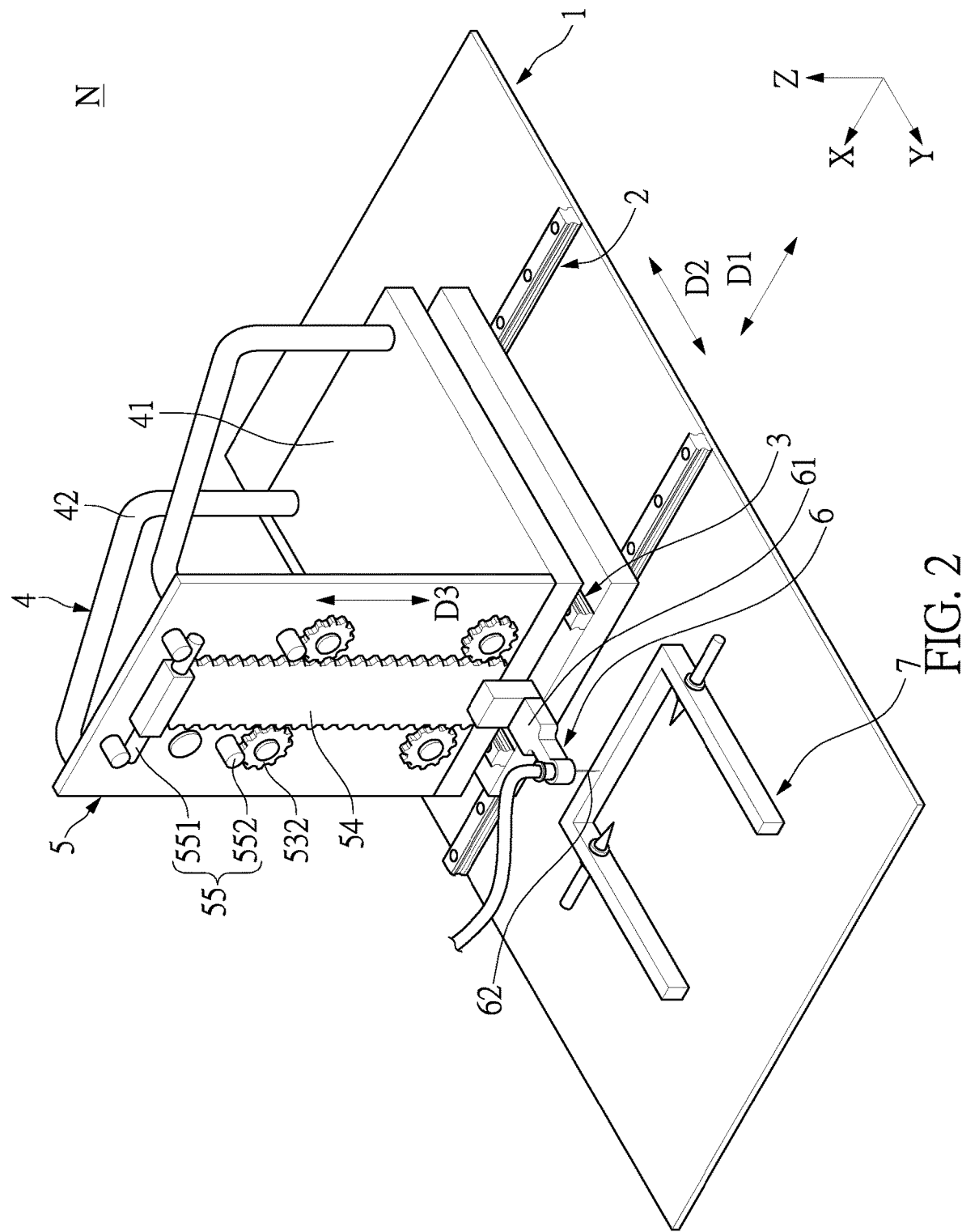
FIG. 2 is another assembled perspective view of the first embodiment of the stereotactic device according to the present disclosure.

Referring to FIGS. 1 and 2, in a first embodiment of the present disclosure, a stereotactic device N is provided for purposes such as drug injection into a test subject M (e.g., the lab mouse shown in FIG. 5), sample collection, or biopsy. More specifically, the stereotactic device N includes a base seat 1, a first moving module 2, a second moving module 3, a supporting module 4, an operating module 5, and a piercing module 6. The first moving module 2 can be disposed on the base seat 1 and can move horizontally back and forth along a first direction D1. The second moving module 3 can be disposed on the first moving module 2 and can move horizontally back and forth along a second direction D2. In addition, the supporting module 4 can be disposed on the second moving module 3, and the operating module 5 can be disposed on the supporting module 4, such that the supporting module 4 and the operating module 5 can move back and forth along the first direction D1 or the second direction D2 via the first and second moving modules 2, 3.

Figure 3:
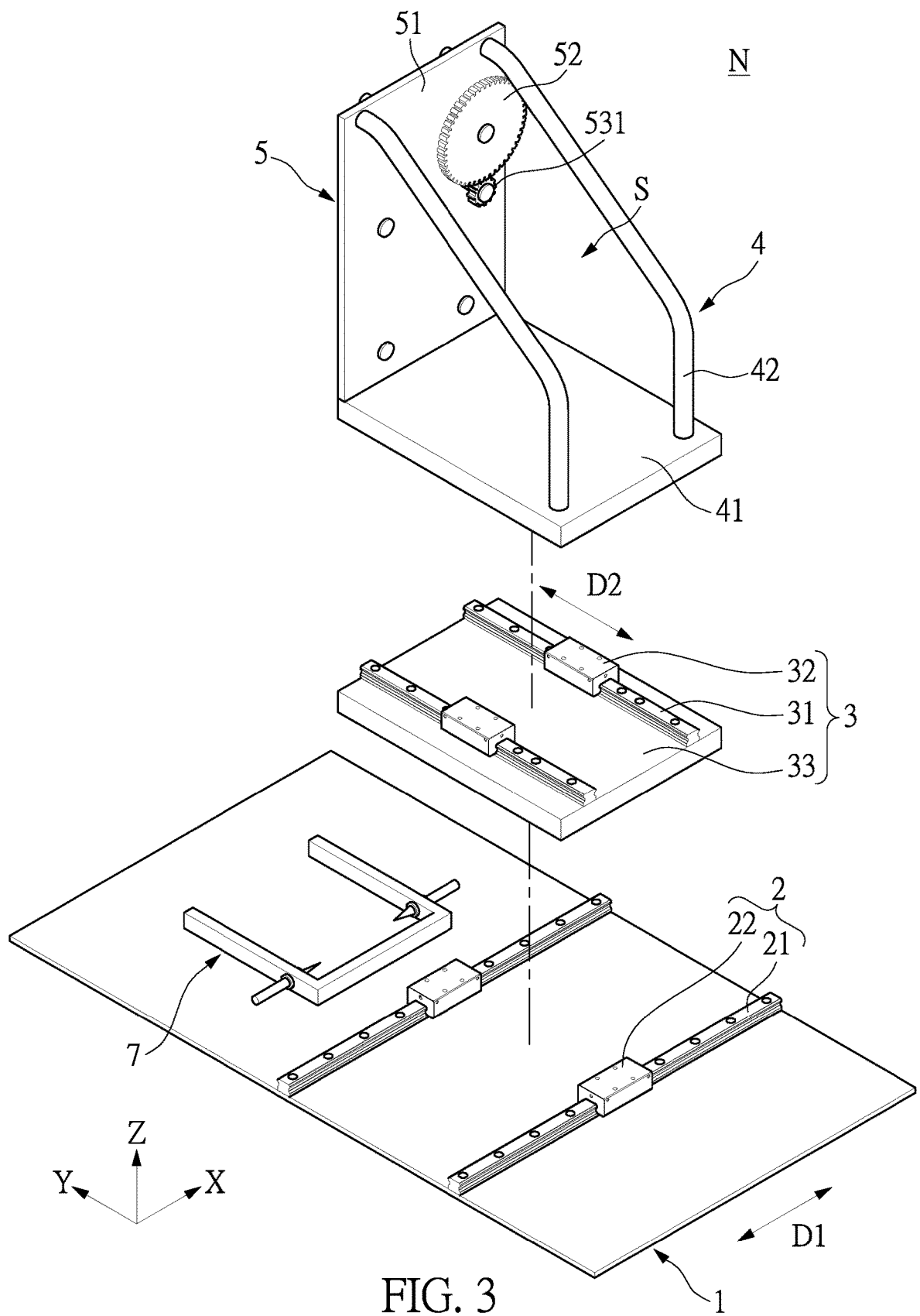
FIG. 3 is an exploded perspective view of the first embodiment of the stereotactic device according to the present disclosure.
Figure 4:
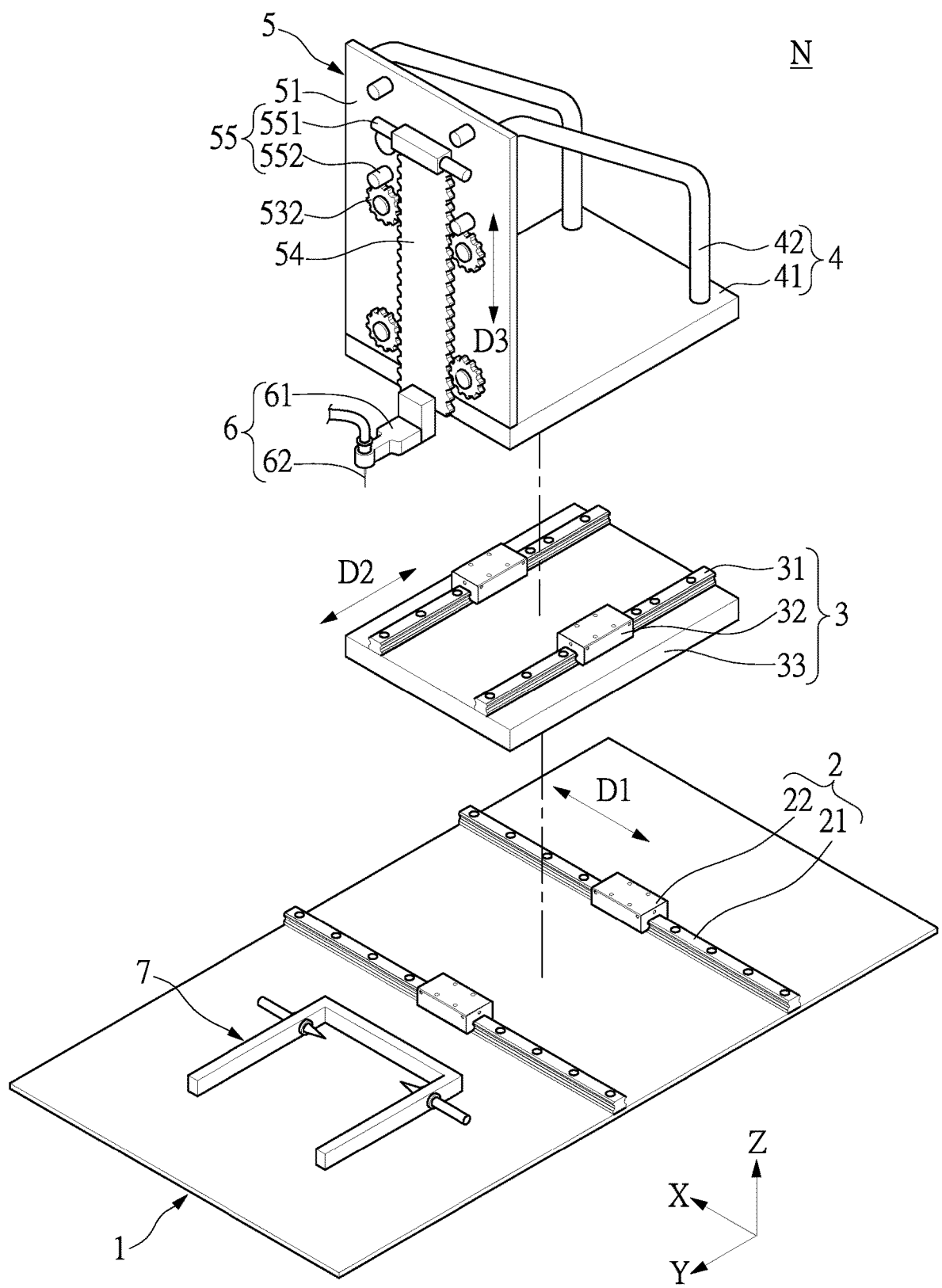
FIG. 4 is another exploded perspective view of the first embodiment of the stereotactic device according to the present disclosure.

Referring to FIGS. 3 and 4, in an exemplary example of the first embodiment of the present disclosure, the first moving module 2 includes a first slide rail 21, and a first slide block 22 disposed on the first slide rail 21. The first moving module 2 is thereby able to move on the base seat 1 along the first direction D1 by virtue of the first slide rail 21 and the first slide block 22. In addition, the second moving module 3 includes a second slide rail 31, and a second slide block 32 disposed on the second slide rail 31. The second slide rail 31 can be disposed on a base 33 of the second moving module 3 so that the second slide rail 31 is indirectly disposed on the first slide block 22 through the base 33. It should be noted, however, that the second slide rail 31 can also be directly disposed on the first slide block 22 in other embodiments of the present disclosure, and is not limited to the configuration disclosed herein. It should also be noted that while the structural configuration of the present embodiment is exemplified as using slide rails and slide blocks, cogwheels and/or cog racks may also used to serve the similar purposes, as long as the first and second moving modules 2, 3 are able to move along the first and second directions D1, D2. In addition, the first and second directions D1, D2 are exemplified as being substantially perpendicular to each other in the present disclosure, so that the supporting module 4 and the operating module 5 are able to move back and forth along a plane formed by the first and second directions D1, D2.

Further referring to FIGS. 1 through 4, the supporting module 4 is disposed on the second slide block 32 of the second moving module 3, and includes a supporting unit 41 and a grip unit 42 disposed on the supporting unit 41. The grip unit 42 allows a user to grip and/or exert force thereon with his/her hands. The grip unit 42 moves together with the supporting unit 4 along the first or second directions D1, D2 in response to a force exerted along one of the two directions, such that the operating unit 5 disposed on the supporting module 4 can also be moved to an appropriate position via manual guidance.

Further referring to FIGS. 1 and 2, the operating module 5 includes a support unit 51, a rotating unit 52 that is disposed on the support unit 51, a driving unit 53 that is disposed on the support unit 51 and that rotates synchronously with the rotating unit 52, and a sliding unit 54 that moves (i.e., displaces) synchronously with the driving unit 53. Exemplarily, in a configuration where the stereotactic device N is being used for drug injection purposes, the stereotactic device N can further include a piercing module 6 that is disposed on the sliding unit 54, such that the piercing module 6 can be driven by the movement of the sliding unit 54 to move back and forth along a third direction D3 and between an initial position and an injection position. The piercing module 6 can include a needle seat 61 disposed on the slide rail 54, and a needle 62 disposed on the needle seat 61. However, it should be noted that the configuration for drug injection in the present disclosure is merely an exemplification for illustrative purposes, and should not be considered as limiting the scope of the present disclosure. In other configurations of the present disclosure, the user may replace the needle 62 with other surgical tools such as scalpels, sampling tools, ultrasonography transducer, etc., without departing from the scope of the present disclosure.

Figure 5:
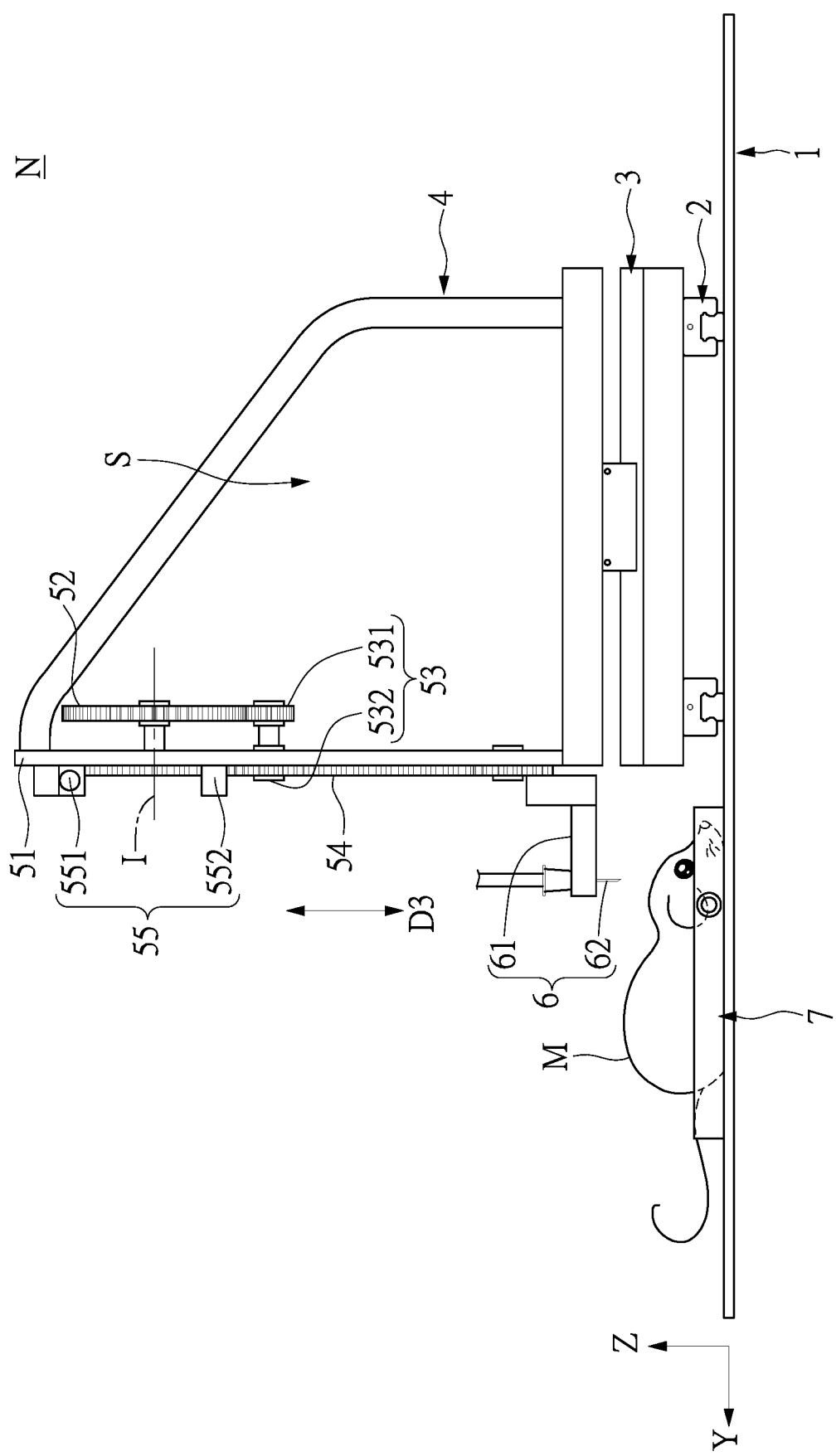
FIG. 5 is a side view illustrating the first embodiment of the stereotactic device according to the present disclosure in operation.
Figure 6:
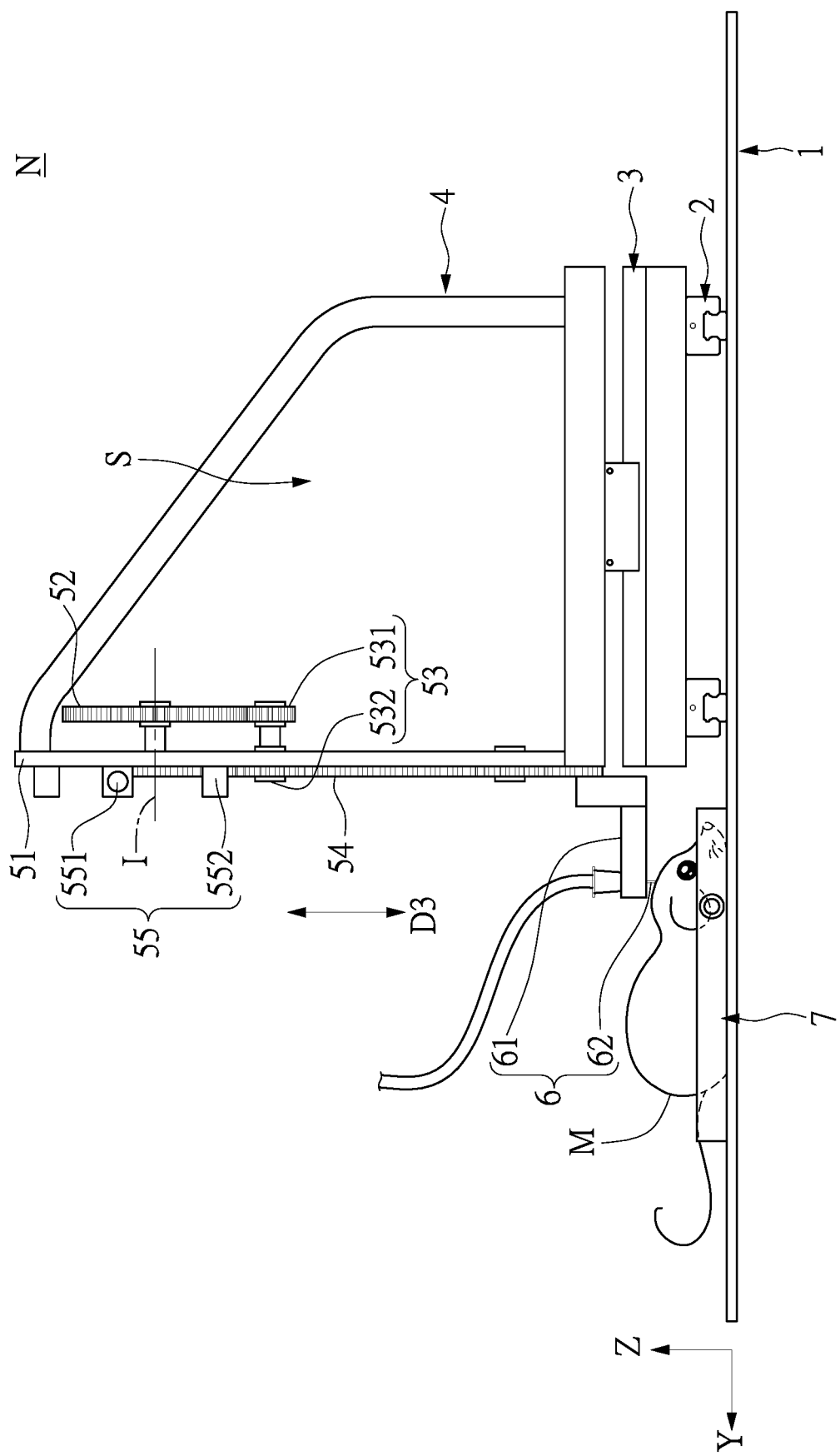
FIG. 6 is another side view illustrating the first embodiment of the stereotactic device according to the present disclosure in operation.

Referring to FIGS. 5 and 6, and further referring to FIGS. 1 and 2, the stereotactic device N further includes a fixing module 7 in this exemplary embodiment of the present disclosure. FIG. 5 shows the piercing module 6 at the initial position, while FIG. 6 shows the piercing module 6 at the injection position. The fixing module 7 is disposed on the base seat 1 to fix the test subject M in position. For example, when the piercing module 6 is applied for injecting a drug into a brain of the test subject M, the fixing module 7 can be used to secure the skull of the test subject M in position. In addition, an anesthetic gas module (not shown in the figures) may be disposed near the fixing module 7 to provide inhalation anesthetics to the test subject M throughout the surgical process.

Further referring to FIGS. 1, 2, 5 and 6, details on the movement mechanics of the operating module 5 will be described in the following. In this embodiment, the piercing module 6 disposed on the sliding unit 54 can move between the initial position and the injection position by way of the rotation of the rotating unit 52 and the driving unit 53. More specifically, the user can use his/her index finger and/or thumb to drive the rotating unit 52, which generates a synchronous rotation of the driving unit 53 so that the piercing module 6 is indirectly driven to move along the third direction D3. In other words, the user can grip the grip unit 42 with one hand and control the movement of the piercing module 6 with fingers of the same hand, thereby improving the sensitivity and precision of the operation. In this embodiment, the rotating unit 52, the driving unit 53, and the sliding unit 54 are cogwheels or cog racks that mesh with each other in sequence to generate synchronous movement thereof. It should be noted, however, that although the foregoing components are exemplified as spur gears in the accompanying figures of the present invention, they may also be helical gears, worms, or worm gears, and are not limited to that disclosed in the present disclosure.

Further referring to FIGS. 1 and 2, the driving unit 53 includes a first driving member 531, and a second driving member 532 that is co-movable (i.e., rotatable in synchrony) with the first driving member 531. The first and second driving members 531, 532 are respectively disposed on two opposite sides of the support unit 51, and are synchronously rotatable and connected by a connecting member (not shown in the figures) that is disposed therebetween and that passes through the support unit 51. The rotating unit 52 meshes or connects with the first driving member 531, and the second driving member 532 meshes or connects with the sliding unit 54. The rotation of the rotating unit 52 directly drives the first driving member 531 to rotate, which drives the second driving member 532 into synchronous rotation, and which indirectly drives the sliding unit 54 into movement. In this manner, the sliding unit 54 can move along the third direction D3 relative to the support unit 51. It is worth noting that, as shown in FIG. 2, a plurality of the second driving members 532 can be included in this embodiment of the present disclosure, but is not limited thereto. One of the second driving members 532 can be co-movably connected to the first driving member 531 to drive the sliding unit 54, while the other ones of the second driving members 532 can respectively be disposed around and meshed with the sliding unit 54, i.e. a cog rack in this embodiment, so as to limit the direction and increase the stability of the movement of the sliding unit 54. In other embodiments of the present disclosure, various other gears or elements can be configured to limit the direction and increase the stability of the movement of the sliding unit 54.

Further referring to FIGS. 2 and 6, the operating module 5 further includes a limiting unit 55 in this exemplary embodiment of the present disclosure. The limiting unit 55 is used to limit the movement of the piercing module 6 disposed on the sliding unit 54. More specifically, the limiting unit 55 includes an abutting member 551 disposed on the sliding unit 54, and at least one limiting member 552 disposed on the support unit 51. The extent of which the piercing module 6 penetrates into the brain of the test subject M can be controlled by having the abutting member 551 abut against one of the limiting members 552 when the sliding unit 54 moves along the third direction D3. It should be noted that, although the limiting member 552 in this embodiment is fixedly disposed on the support unit 51, in other embodiments of the present disclosure, the limiting member 552 can also be of an adjustable type that can adjust the extent of which the piercing module 6 is penetrated into the test subject M according to practical requirements.

In continuance of the above, and further referring to FIGS. 1 and 5, a finger space S can exemplarily be disposed between the grip unit 42 and the operating module 5 to allow fingers of the user to extend thereinto and control the rotating unit 52. In addition, the rotating unit 52 can have a rotational axis I that is substantially perpendicular to the third direction D3, so that when the user rotates the rotating unit 52, a force exerted upon the rotating unit 52 is substantially parallel to the movement direction of the piercing module 6. Therefore, the above configuration allows the user to receive a direct tactile feedback when operating the stereotactic device N. Furthermore, when the needle 62 is driven by the rotating unit 52 to pierce to an appropriate position in the test subject M, the user can manually squeeze the injector or utilize an automatic injector to introduce the drug into the test subject M through the needle 62. It should be noted, however, that in other embodiments of the present disclosure, the rotational axis I can also be non-perpendicular to the third direction D3, so that an angle of 60° to 90° exists between the rotational axis I and the third direction D3, or so that the rotational axis I is parallel to the third direction D3. In addition, the angle of the rotational axis I can be varied to accommodate practical requirements such as those in consideration of ergonomics or finger manipulation.

Figure 7:
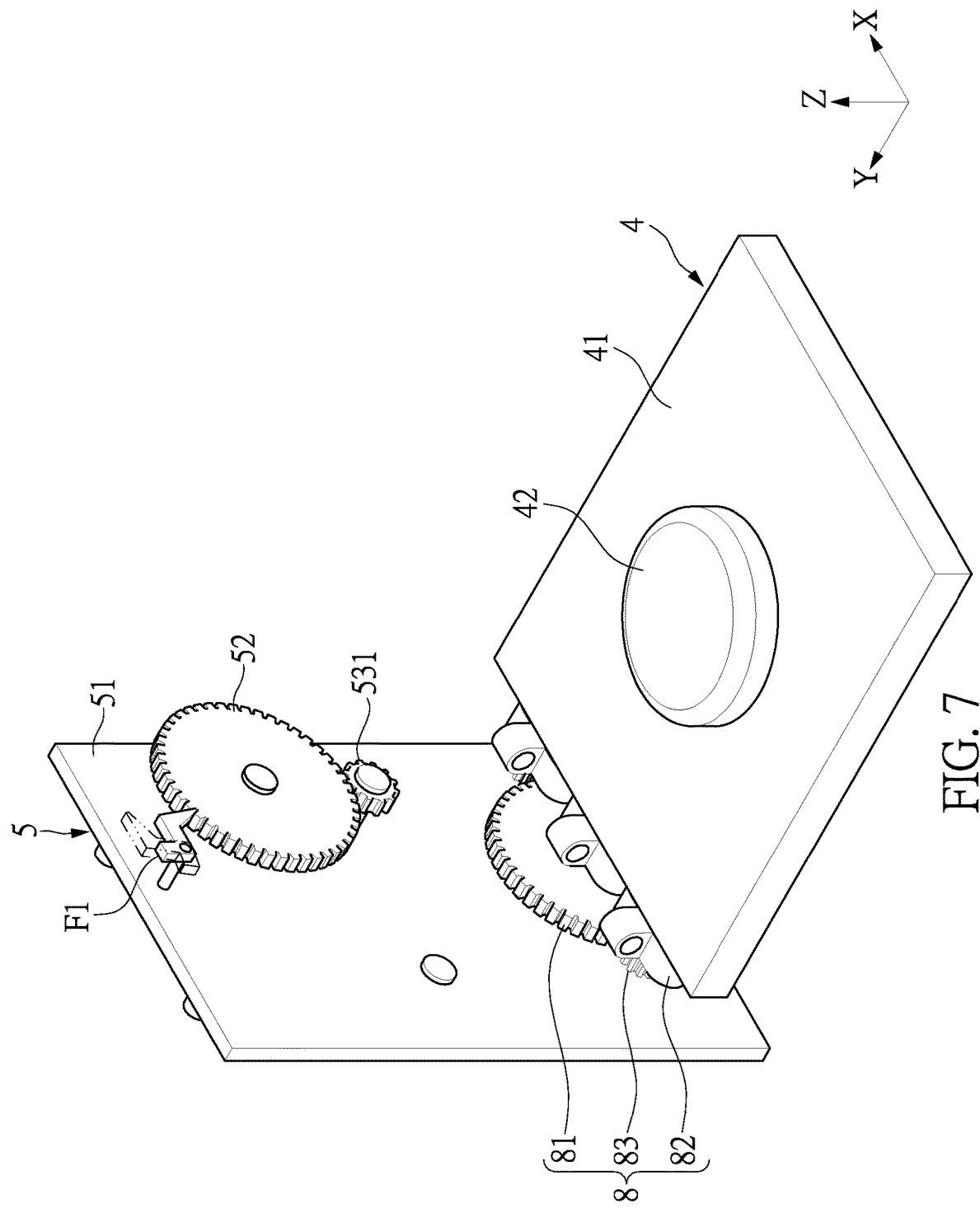
FIG. 7 is a schematic perspective view showing a supporting module and an operating module of a second embodiment of the stereotactic device according to the present disclosure in an assembled state.
Figure 8:
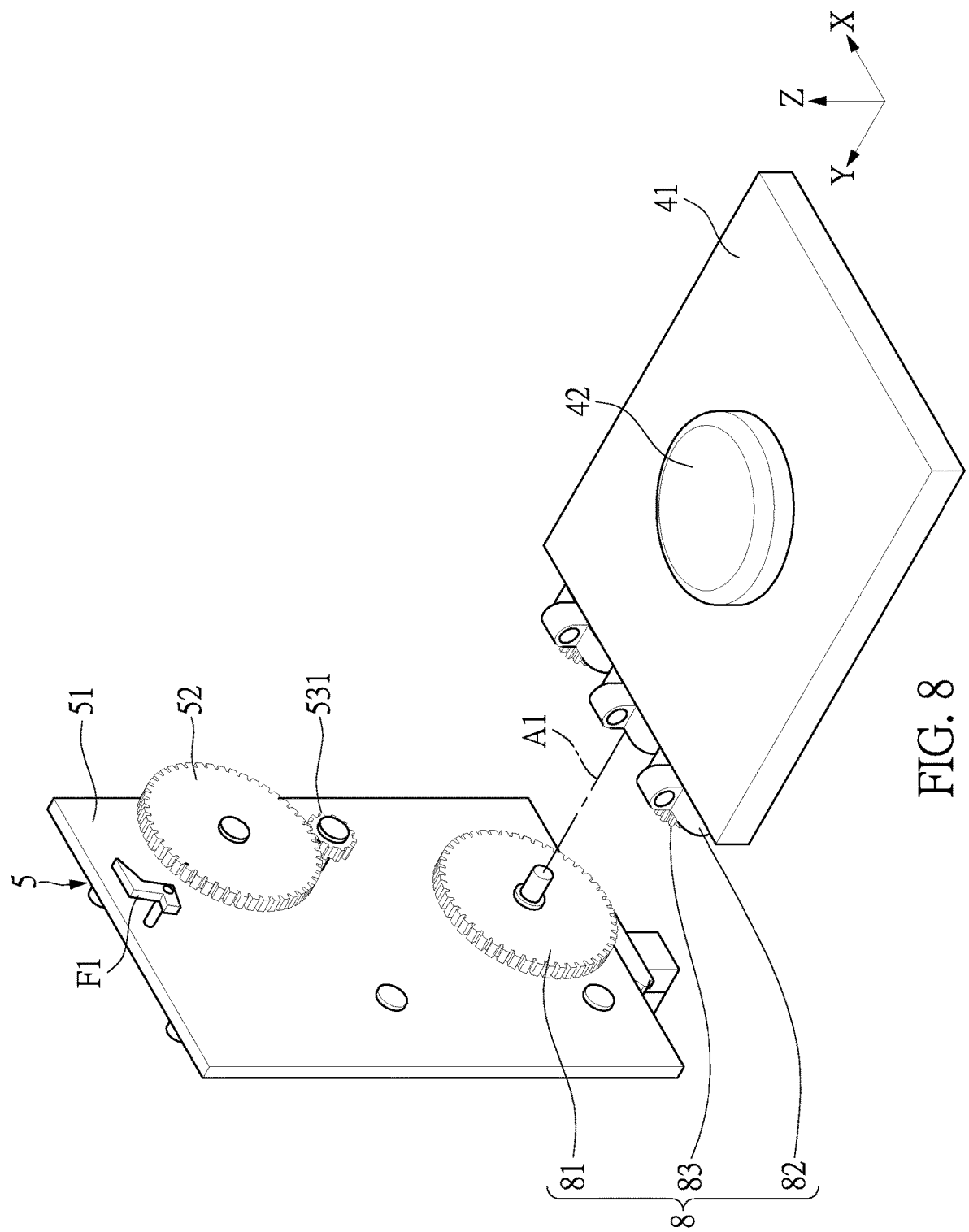
FIG. 8 is a perspective view showing the supporting module and the operating module of the second embodiment of the stereotactic device according to the present disclosure in a disassembled state.
Figure 9:
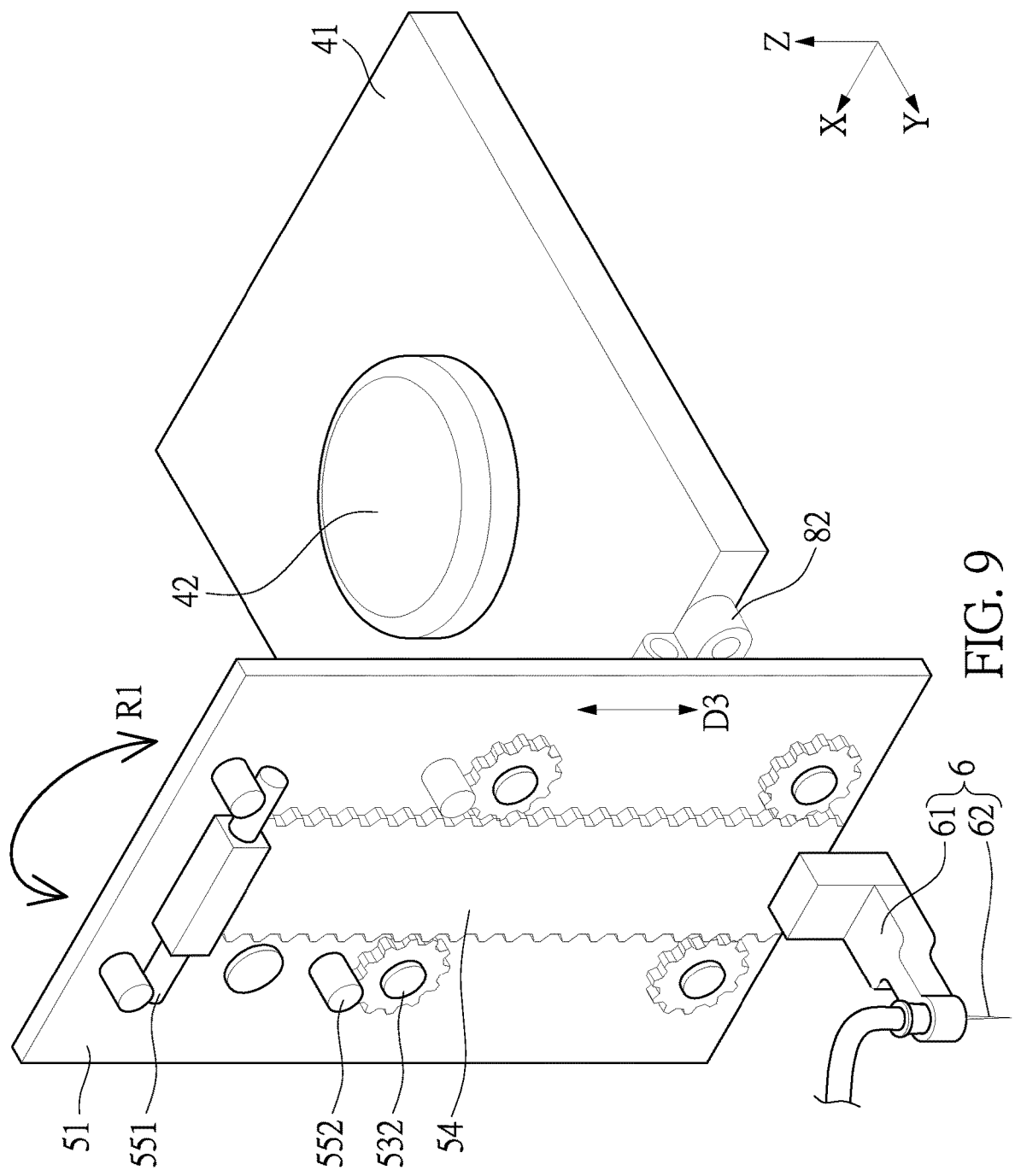
FIG. 9 is another assembled perspective view showing the supporting module and the operating module of the second embodiment of the stereotactic device according to the present disclosure.

Reference is made to FIGS. 7 through 9, which show a second embodiment of the present disclosure. While the structural features of the stereotactic device N of the second embodiment are essentially similar to those of the first embodiment, certain differences distinguishing the former from the latter (as a comparison of FIG. 7 and FIG. 1 would reveal) are described as follows. In the second embodiment, the stereotactic device N further includes a first rotating module 8. With the disposition of the first rotating module 8, the operating module 5 of the second embodiment can rotate relative to the supporting module 4, e.g. rotate in a direction perpendicular to the plane formed by the first direction D1 and the second direction D2 (i.e., the X-Y plane), but is not limited thereto. In other embodiments of the present disclosure, the operating module 5 may also rotate in a direction oblique to the X-Y plane. It should further be noted that the rotational direction of the operating module 5 is not limited in any of the subsequent embodiments set forth in the present disclosure.

Reference is further made to FIG. 8, illustrating the structural and operational relationship between the operating module 5 and the supporting module 4. The first rotating module 8 is disposed between the operating module 5 and the supporting module 4, so that the operating module 5 can rotate relative to the supporting module 4. Exemplarily, the first rotating module 8 includes a first rotating unit 81 disposed on the operating module 5, and a first supporting seat 82 disposed on the supporting unit 41 of the supporting module 4. The first rotating unit 81 is fixed on the support unit 51 and connected to the first supporting seat 82, and has a first rotational axis A1. The operating unit 5 can rotate around the first rotational axis A1 relative to the first supporting seat 82 via the first rotating unit 81. Exemplarily, in order to provide increased stability to the rotation of the operating module 5, the first rotating module 8 can further include a second rotating unit 83. The second rotating unit 83 is disposed on the first supporting seat 82 and meshed or connected with the first rotating unit 81, such that the first rotating unit 81 can rotate relative to the second rotating unit 83.

Referring to FIGS. 8 through 11, the first supporting seat 82 of the first rotating module 8 and the supporting unit 41 of the supporting module 4 can be formed as one piece, but is not limited thereto. For example, the first supporting seat 82 and the supporting unit 41 in any of the subsequent embodiments may be separate from each other. Furthermore, the grip unit 42 can be omitted from the supporting module 4 of the second embodiment, so that the user can place an ulnar side of a palm on the supporting unit 41 and rotate the rotating unit 52 with one or more fingers of the same hand. In addition, the design of the grip unit 42 is not limited to that disclosed in the first embodiment of the present disclosure, and can also be designed as a protrusion disposed on the supporting unit 41 to support a grasp of the user. The primary function of the grip unit 42 of this embodiment is to facilitate a push or pull operation of the supporting module 4 for movement along the first or second directions D1, D2. In other words, in such configurations, the grip unit 42 may be considered as part of the supporting unit 41.

Figure 10:
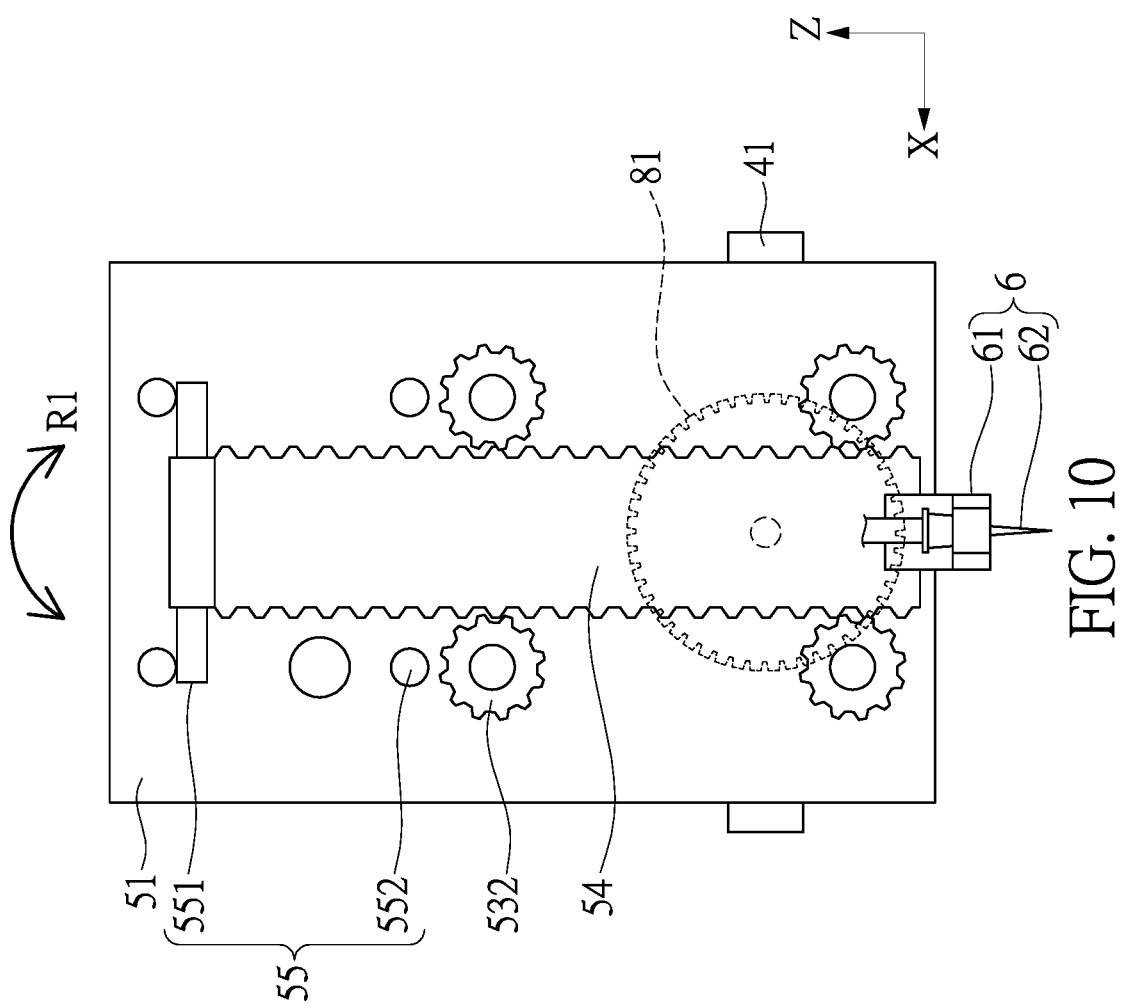
FIG. 10 is a schematic view illustrating the supporting module and the operating module of the second embodiment of the stereotactic device according to the present disclosure in operation.
Figure 11:
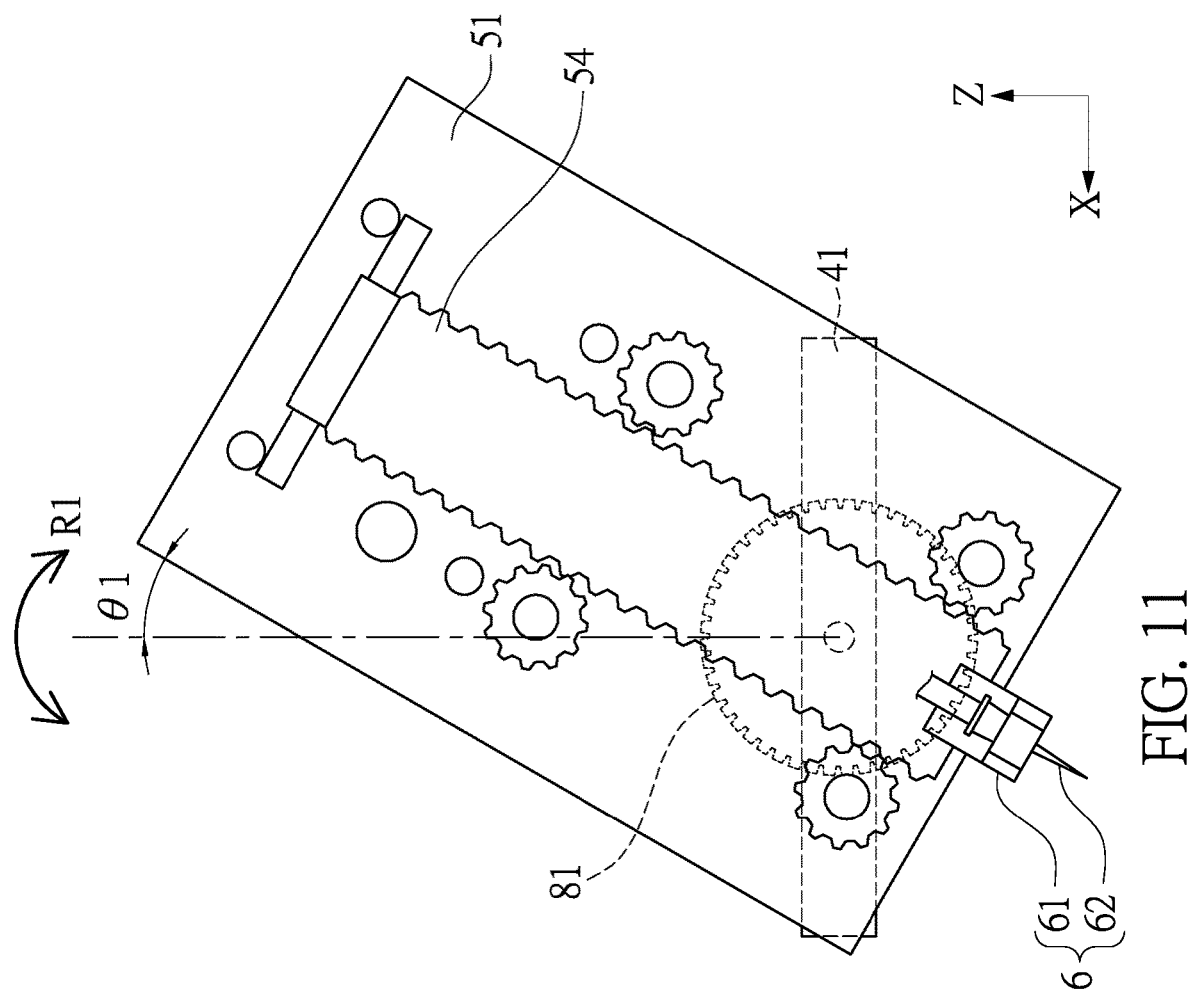
FIG. 11 is another schematic view illustrating the supporting module and the operating module of the second embodiment of the stereotactic device according to the present disclosure in operation.

Reference is next made to FIGS. 10 and 11, with further reference made to FIGS. 7 and 9. In a more specific description of the supporting module 4 and the operating module 5 of the second embodiment, the operating module 5 can rotate back and forth relative to the supporting module 4 in a first rotational direction R1 by virtue of the first rotating module 8. For example, the operating module 5 can rotate to a first predetermined angle θ1 that ranges between 0° to 75°, but is not limited thereto. In addition, the stereotactic device N can further include a first switch F1 that is disposed on the support unit 51 and that restricts movement of the rotating unit 52. When the needle 62 is driven by the rotating unit 52 and pierces to an appropriate position in the test subject M, the first switch F1 such as that shown in FIG. 7 can be employed to fix the rotating unit 52 in position, such that the position of the needle 62 relative to the test subject M is also fixed. The user can then proceed to commence the drug injection procedures via the piercing module 6. Furthermore, the first switch F1 of FIG. 7 can move relative to the support unit 51 to abut against or detach from the rotating unit 52, thereby catching or releasing the rotating unit 52. More specifically, the first switch F1 can pivot about the support unit 51 so that an end thereof (not labeled in the figures) can abut against the teeth of the rotating unit 52 to restrict movement of the rotating unit 52.

Figure 12:
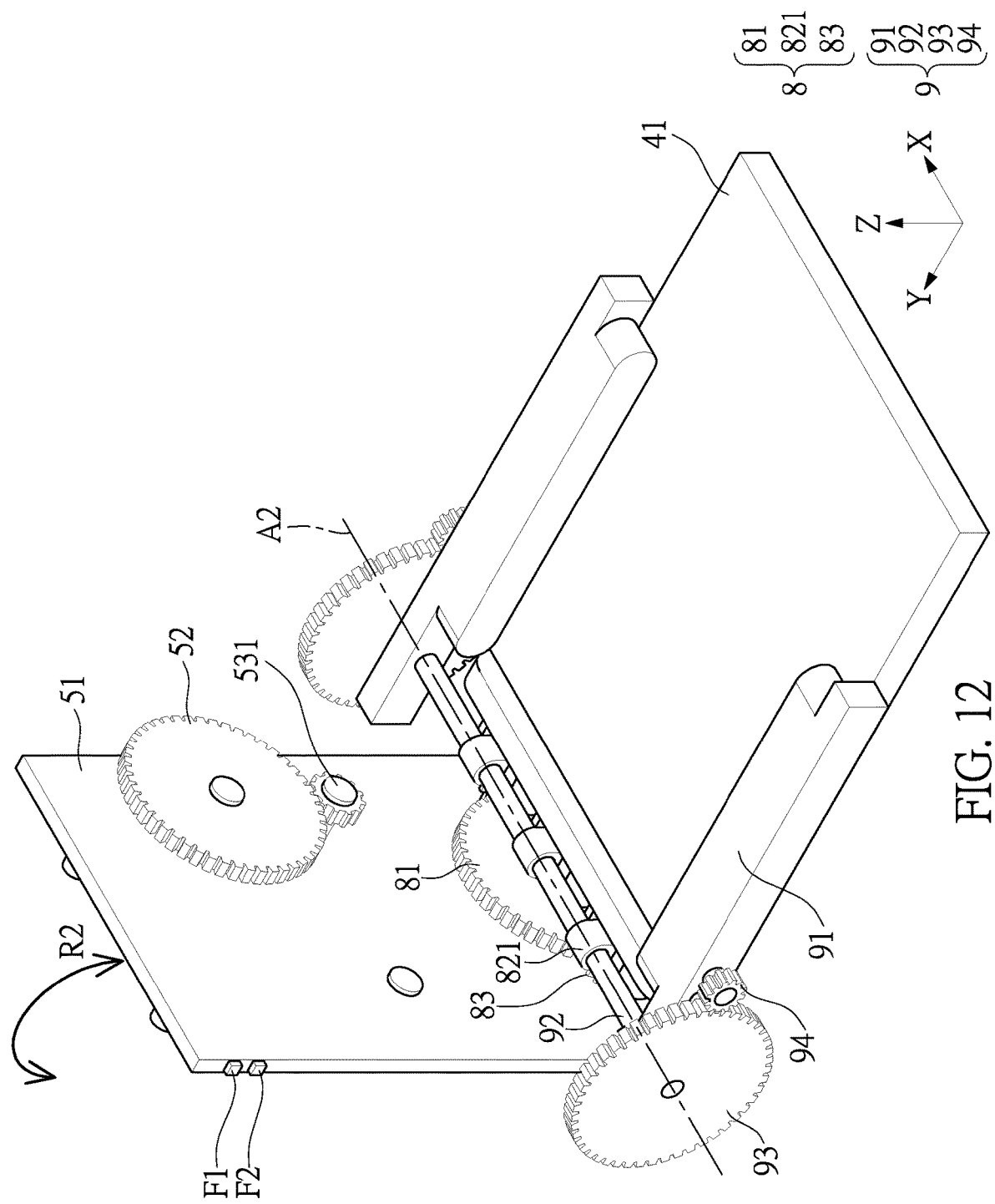
FIG. 12 is a perspective view showing the supporting module and the operating module of a third embodiment of the stereotactic device according to the present disclosure in an assembled state.
Figure 13:
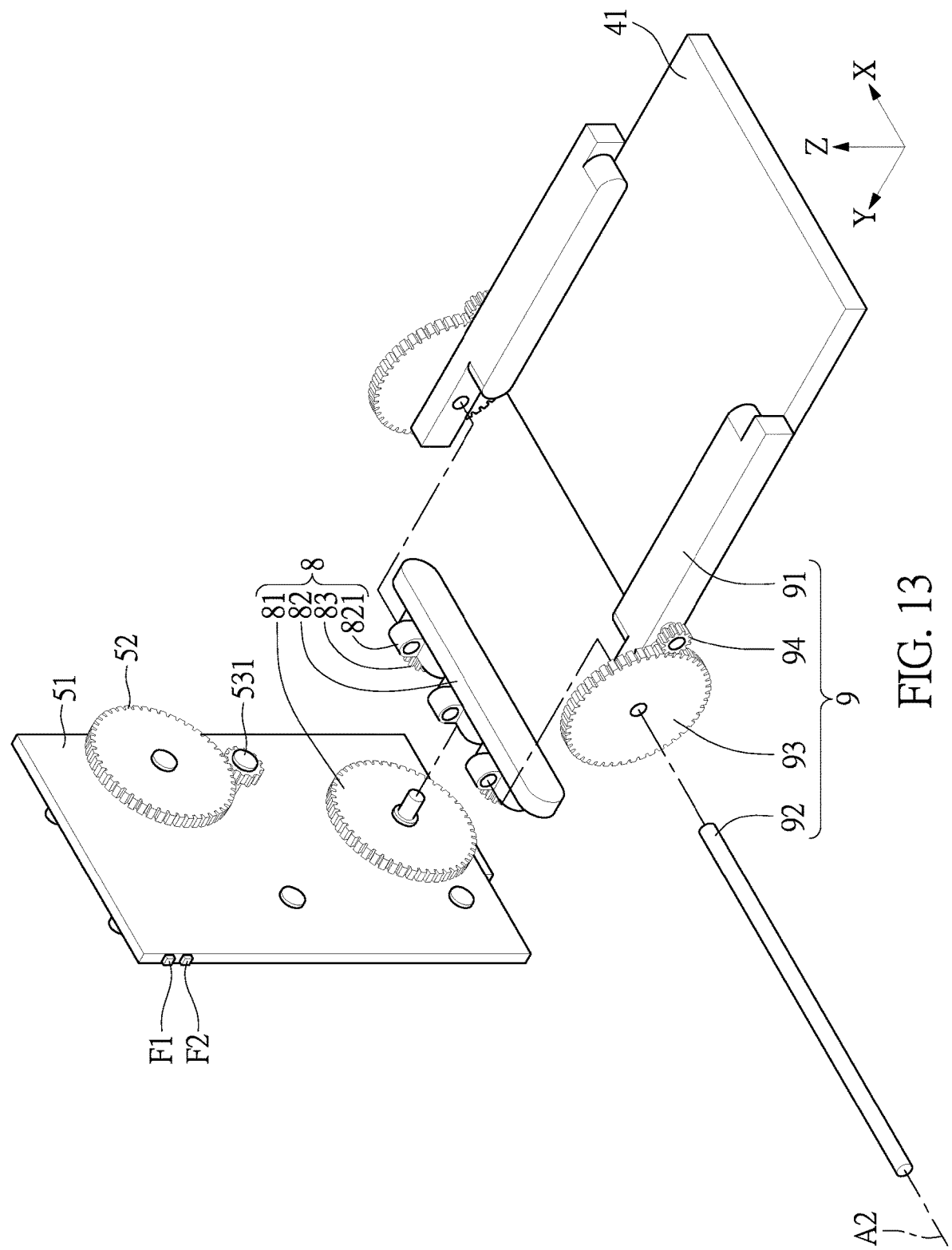
FIG. 13 is a perspective view showing the supporting module and the operating module of the third embodiment of the stereotactic device according to the present disclosure in a disassembled state.

Reference is made to FIGS. 12 and 13, which show a third embodiment of the present disclosure. While the structural features of the stereotactic device N of the third embodiment are essentially similar to those of the second embodiment, certain differences distinguishing the former from the latter (as a comparison of FIG. 12 and FIG. 7 would reveal) are described as follows. The stereotactic device N of the third embodiment further includes a second rotating module 9. With the disposition of the second rotating module 9, the operating module 5 of the third embodiment can rotate along a second rotational direction R2, e.g., on the Y-Z plane, relative to the supporting module 4. It should be noted that the first rotating module 8 and the second rotating module 9 can move in synchrony with each other so that the operating module 5 can move concurrently along both of the first and second rotational directions R1, R2.

Further referring to FIG. 13, the second rotating module 9 is disposed between the first rotating module 8 and the supporting module 4, and the operating module 5 rotates along the second rotational direction R2 relative to the supporting module 4 via the second rotating module 9. Exemplarily, the second rotating module 9 of the third embodiment includes a second supporting seat 91 disposed on the supporting module 4, and a pivot axle 92 disposed on the second supporting seat 91. The pivot axle 92 has a second rotational axis A2, and the first rotating module 8 is pivotally connected to the pivot axle 92 so as to rotate along the second rotational axis A2 relative to the second rotational module 9. Therefore, the operating module 5 disposed on the first rotating module 8 can be driven by the second rotating module 9 to rotate along the second rotational direction R2. In this embodiment, the first rotational direction R1 is substantially perpendicular to the second rotational direction R2.

In continuance of the above, and further referring to FIG. 13, the second rotating module 9 can further include a first pivoting unit 93 disposed on the pivot axle 92, and a second pivoting unit 94 that meshes or connects with the first pivoting unit 93. With the disposition of the first pivoting unit 93 and the second pivoting unit 94, the stability of the second rotating module 9 of the third embodiment can be improved. In addition, the first supporting seat 82 can further include a pivoting portion 821 on which the pivot axle 92 pivots. In this embodiment, the first supporting seat 82 and the supporting unit 41 are separate from each other, so that the first supporting seat 82 can rotate relative to the second supporting seat 91 and the supporting unit 41. The second supporting seat 91 and the supporting unit 41 of this embodiment can be formed as one piece, but is not limited thereto.

Figure 14:
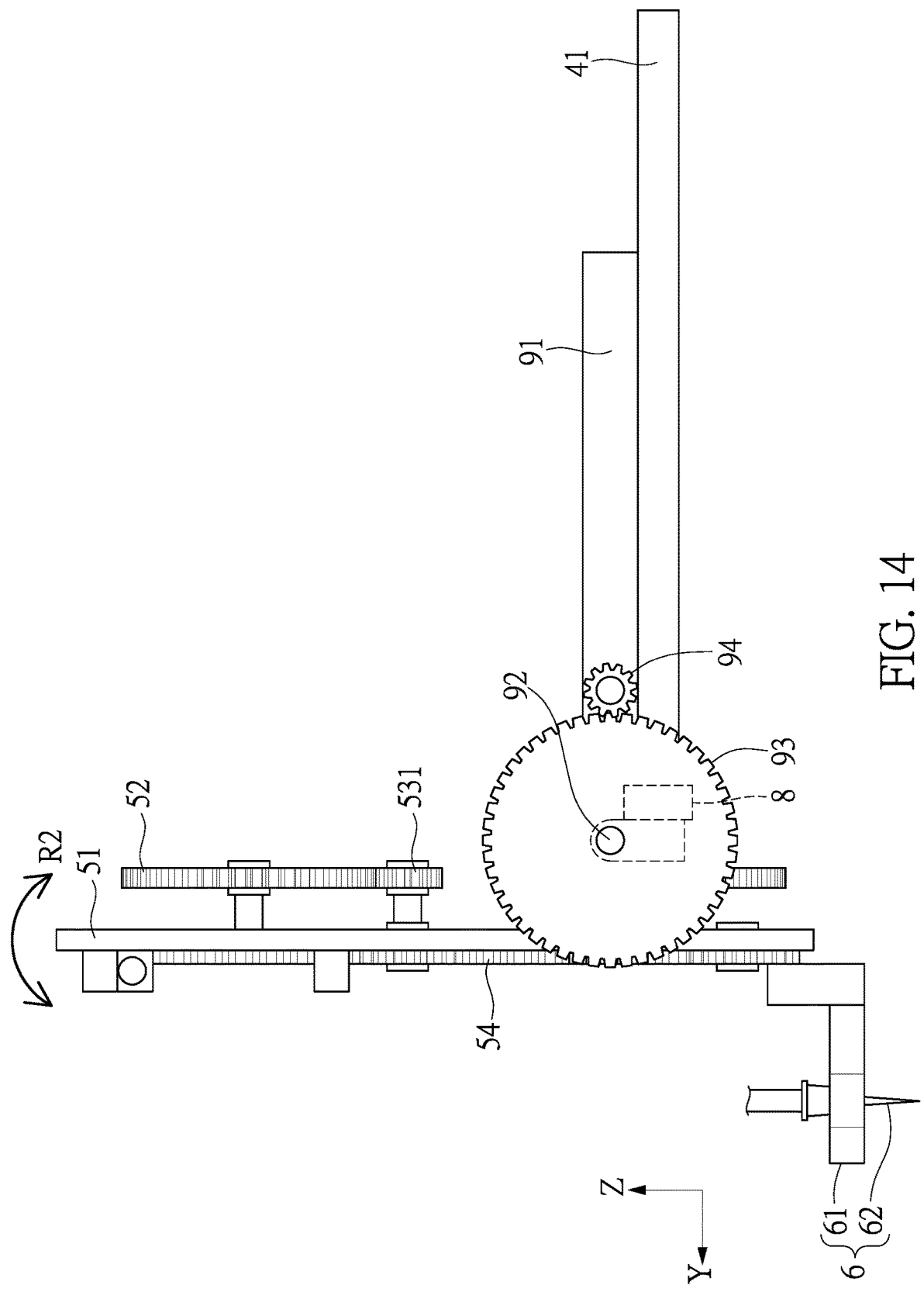
FIG. 14 is a schematic view illustrating the supporting module and the operating module of the third embodiment of the stereotactic device according to the present disclosure in operation.
Figure 15:
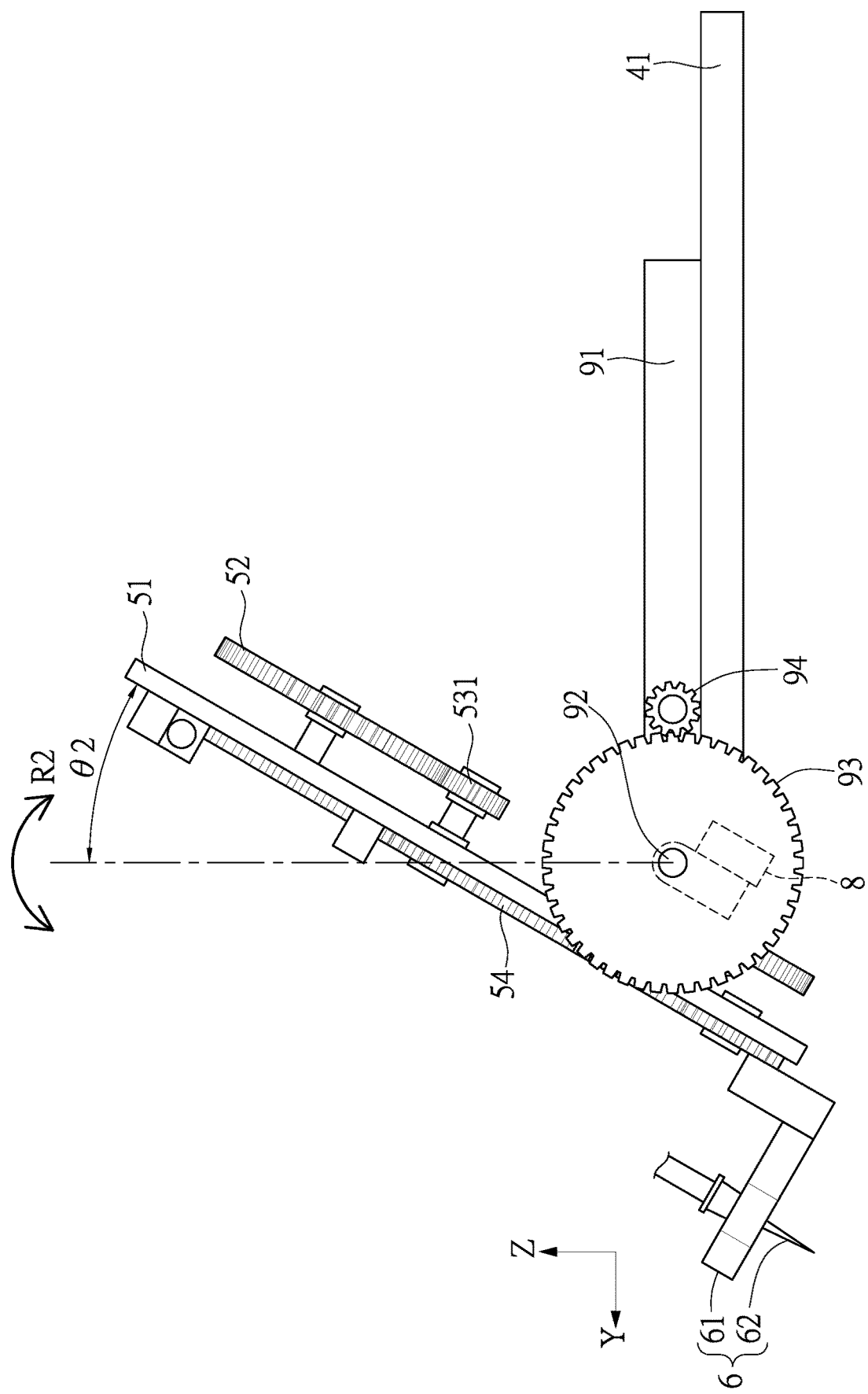
FIG. 15 is another schematic view illustrating the supporting module and the operating module of the third embodiment of the stereotactic device according to the present disclosure in operation.

Referring to FIGS. 14 and 15, and further referring to FIG. 12, the inclusion of the second rotating module 9 allows the operating module 5 to rotate along the second rotational direction R2 relative to the supporting module 4. The rotation angle of the operating module 5 can be a second predetermined angle θ2 that ranges between 0° to 60°, but is not limited thereto. In addition, the stereotactic device N of the third embodiment can further include a first switch F1 and a second switch F2, such as those shown in FIGS. 12 and 13. In this embodiment, the first and second switches F1, F2 are disposed on the support unit 51 and are electrical switches that respectively control the movability of the rotating unit 52 and the first and second rotating modules 8, 9. For example, when the operating module 5 moves to an appropriate position via the first and second moving modules 2, 3, the second switch F2 can be pressed to fix the operating module 5 in position. Then, when the piercing module 6 is moved to an appropriate position via the rotating unit 52, the first switch F1 can be activated to restrict movement of the rotating unit 52 so as to facilitate subsequent drug injecting procedures into the test subject M.

In continuance of the above, the stereotactic device N of the third embodiment can further include a control module (not shown in the figures), and the rotating unit 52, the first rotating module 8, and the second rotating module 9 can be magnetic structures including electromagnetic valves or other magnetic elements (such as those used for fixing slide rails/slide blocks in place by way of the electromagnetic braking principle), but is not limited thereto. The control module of this embodiment is electrically connected to the first and second switches F1, F2, and may also be electrically connected to the rotating unit 52, the first rotating module 8, and the second rotating module 9. In this way, the first and second switches F1, F2 can respectively control the movability of the rotating unit 52 and the first and second rotating modules 8, 9. It should be noted that the third embodiment can further include other switches to control electromagnetic-brakeable slide rails that can replace the first and second moving modules 2, 3.

Figure 16:
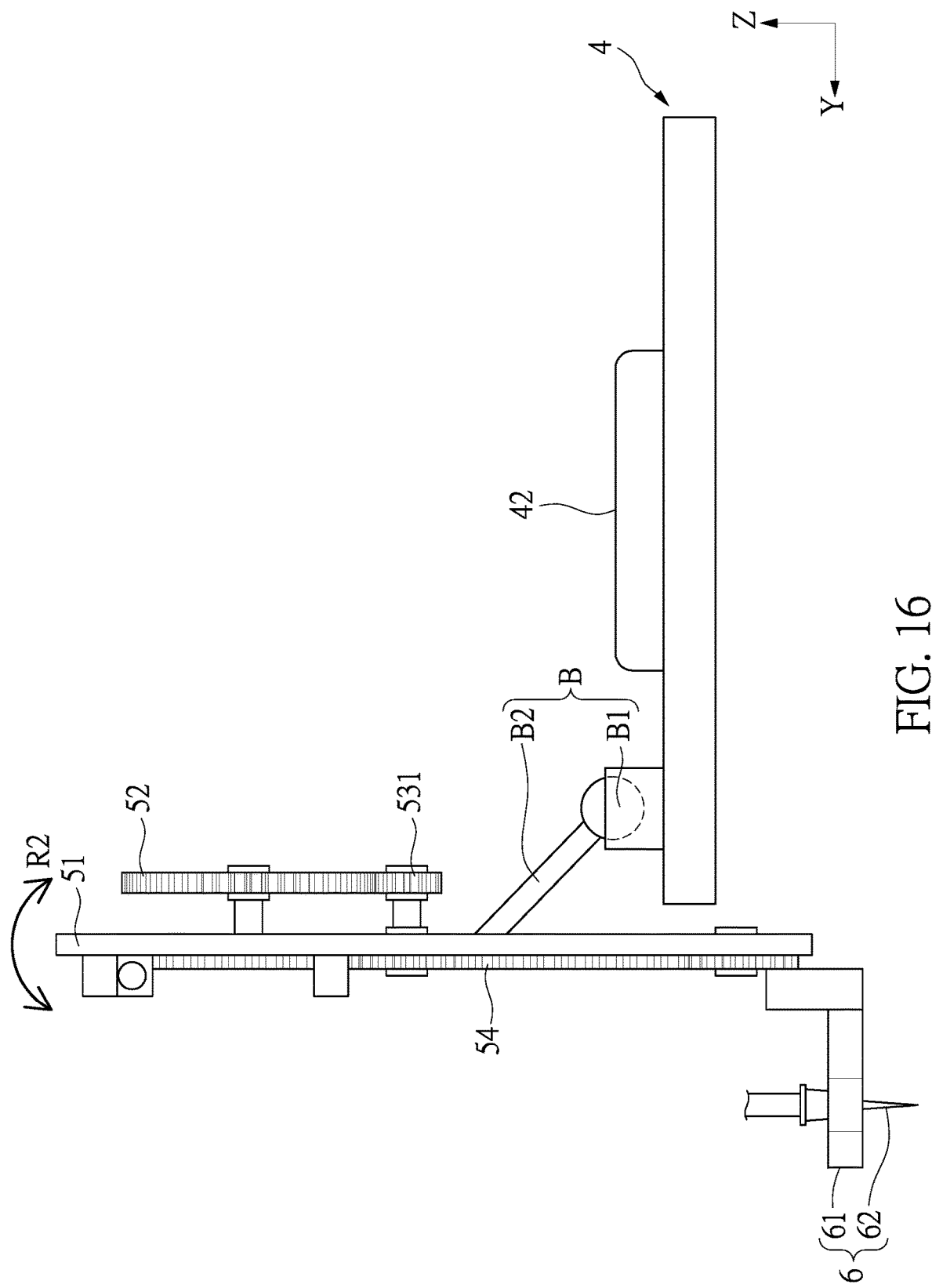
FIG. 16 is a schematic side view showing the supporting module and the operating module of a fourth embodiment of the stereotactic device according to the present disclosure.

Reference is made to FIG. 16, which illustrates a fourth embodiment of the present disclosure allowing the operating module 5 to rotate concurrently along both of the first and second rotational directions R1, R2. More specifically, the stereotactic device N of the fourth embodiment further includes a rotating module B. The rotating module B includes a first connecting part B1 that is disposed on the supporting unit 41 of the supporting module 4, and a second connecting part B2 that is disposed on the support unit 51 of the operating module 5 and that rotates relative to the first connecting part B1.

In this embodiment, the rotating module B is a universal joint, such as a ball-shaped universal joint. However, in other embodiments of the present disclosure, the rotating module B can also be other types of universal joints, such as a cross shaft universal joint, and is not limited by that disclosed in the present disclosure. Therefore, by virtue of the rotating module B provided in this embodiment, the operating module 5 can rotate concurrently along both the first and second rotational directions R1, R2.

Figure 17:
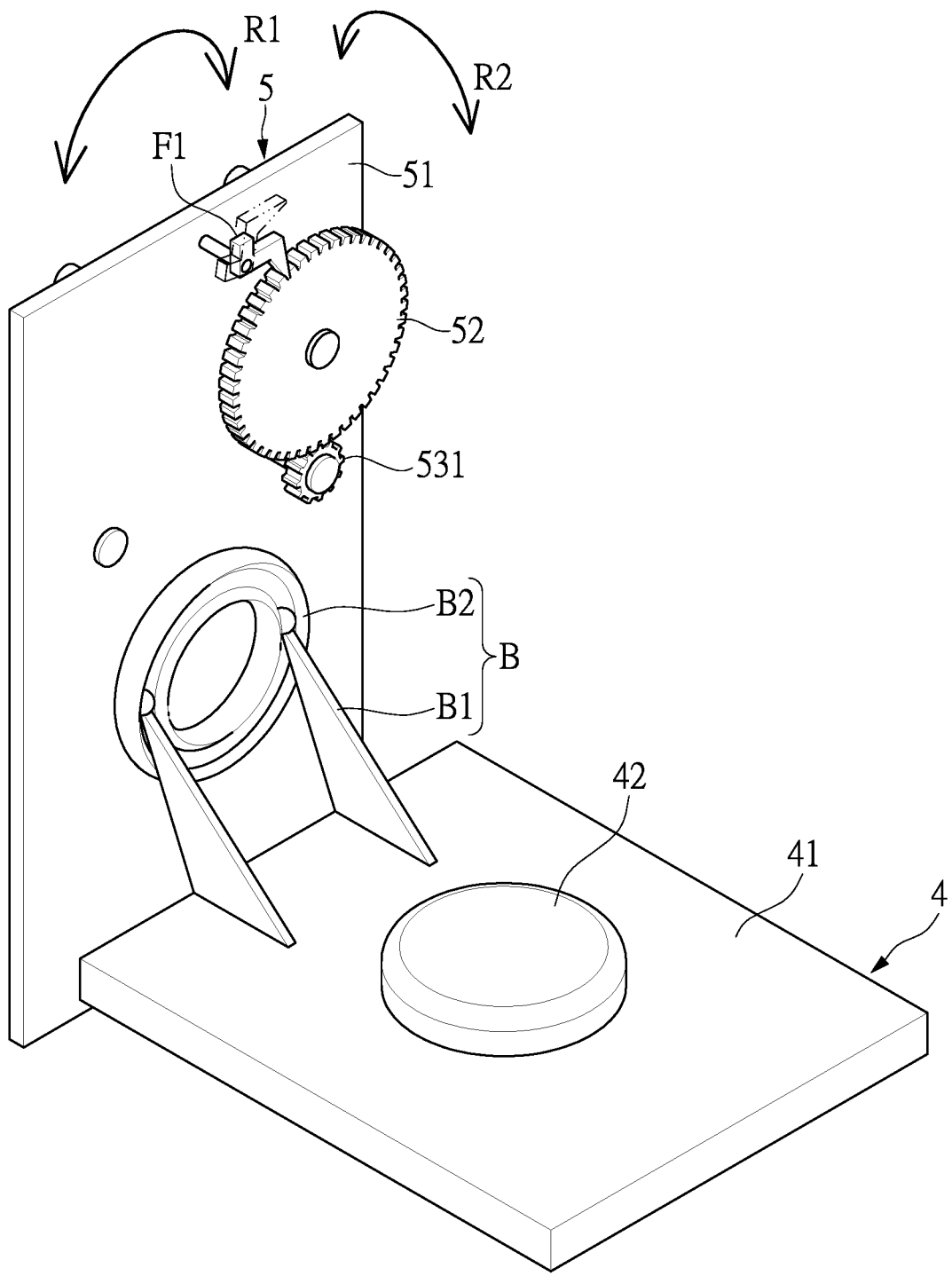
FIG. 17 is a schematic perspective view showing the supporting module and the operating module of a fifth embodiment of the stereotactic device according to the present disclosure.

Reference is made to FIG. 17, which illustrates a fifth embodiment of the present disclosure also allowing the operating module 5 to rotate concurrently along both of the first and second rotational directions R1, R2. More specifically, the stereotactic device N of the fifth embodiment includes a rotating module B. The rotating module B includes a first connecting part B1 that is disposed on the supporting unit 41 of the supporting module 4, and a second connecting part B2 that is disposed on the support unit 51 of the operating module 5 and that rotates relative to the first connecting part B1.

In this embodiment, two of the first connecting parts B1 are correspondingly disposed on the supporting unit 41. Each of the first connecting parts B1 has a ball-shaped end. Furthermore, the second connecting part B2 is a circular tube in which the ball-shaped ends of the first connecting parts B1 can slide relative to the circular tube. In this way, the operating module 5 can rotate concurrently along both of the first and second rotational directions R1, R2. It should be noted that, although the circular tube shown in FIG. 17 is a full circular shape, in other embodiments of the present disclosure, the circular tube can also be shaped in a semi-circle to limit the extent of movement along the first rotational direction R1.

In sum, the effects of the stereotactic device N provided by the present disclosure are that the supporting module 4 can move along the first or second directions D1, D2 by exerting a force upon the grip unit 42 in the first or second directions D1, D2. Furthermore, the user can rotate the rotating unit 52 with fingers of the force-exerting hand to control the movement of the piercing module 6 along the third direction D3. At the same time, the fingers can push or pull upon the operating module 5 to move the piercing module 6 back and forth along the first or second rotational directions R1, R2. In other words, the user can single-handedly control the movement directions of supporting module 4, the operating module 5, and the piercing module 6 to achieve control of multi-axial movement with a single hand.

Furthermore, the stereotactic device N can be applied to surgical operations involving organs other than the brain. Each drug injection process into different organs requires the needle 62 to penetrate through different tissues and reach different depths. Minimally invasive surgeries, for example, do not typically provide a strong level of visual feedback to the user/surgeon. In this case, the tactile feedback provided by the stereotactic device N of the present disclosure could allow the user to perform the surgery without the support of image guidance technology.

Therefore, with the stereotactic device N provided by the present disclosure, a user can freely manipulate the stereotactic device N with one hand to achieve improved sensitivity, stability, precision, and convenience.

While the present disclosure has been described in connection with what are considered the exemplary embodiments, it is understood that the present disclosure is not limited to the disclosed embodiments but is intended to cover various changes, alterations, or modifications included within the spirit and scope of the broadest interpretation so as to encompass all such equivalent arrangements.

What is claimed is:

1. A stereotactic device comprising:
   a base seat;
   a first moving module that is disposed on said base seat and that moves along a first direction;
   a second moving module that is disposed on said first moving module and that moves along a second direction substantially perpendicular to the first direction;
   a supporting module that is disposed on said second moving module and that includes:
      a supporting unit, and
      a grip unit that is disposed on said supporting unit;
      wherein said supporting module moves with said grip unit along one of the first and second directions when a force is exerted along one of the first and second directions on said grip unit;
   an operating module that is disposed on said supporting module and that includes:
      a support unit,
      a rotating unit that is disposed on said support unit,
      a driving unit that is disposed on said support unit and that is co-movable with said rotating unit, and
      a sliding unit that is co-movable with said driving unit; and
   a piercing module that is disposed on said sliding unit, wherein said piercing module moves between an initial position and an injection position via rotation of the rotating unit;
   wherein each of said rotating unit, said driving unit, and said sliding unit is one of a cogwheel and a cog rack;
   wherein said sliding unit of said operating module moves along a third direction, and said rotating unit has a rotational axis that is substantially perpendicular to the third direction;
   wherein a finger space is formed between the grip unit and the operating module to allow a finger to extend thereinto and control the rotating unit.

2. The stereotactic device as claimed in claim 1, wherein said driving unit includes a first driving member, and a second driving member that is co-movable with said first driving member, and wherein said rotating unit is connected to said first driving member, and said second driving member is connected to said sliding unit, such that rotation of said rotating unit drives said first driving member, said second driving member, and said sliding unit in synchrony.

3. The stereotactic device as claimed in claim 1, wherein said first moving module includes a first slide rail that is disposed on said base seat and a first slide block that is slidably disposed on said first slide rail, and said second moving module includes a second slide rail and a second slide block that is slidably disposed on said second slide rail, and wherein said second slide rail is disposed on said first slide block, and said supporting module is disposed on said second slide block.

4. The stereotactic device as claimed in claim 3, wherein said second moving module includes a base, and wherein said second slide rail is disposed on said first slide block via said base.

5. The stereotactic device as claimed in claim 1, wherein said sliding unit of said operating module moves along the third direction that is substantially perpendicular to the first and second directions.

6. The stereotactic device as claimed in claim 1, wherein said operating module further includes a first switch that is disposed on said support unit, that moves relative to said support unit, and that restricts the movement of said rotating unit, said first switch catching said rotating unit when abutting thereagainst, and releasing said rotating unit when detaching therefrom.

7. The stereotactic device as claimed in claim 1, further comprising a first rotating module that is disposed between said operating module and said supporting module, said operating module rotating relative to said supporting module along a first rotational direction via said first rotating module.

8. The stereotactic device as claimed in claim 7, wherein said first rotating module includes a first rotating unit that is disposed on said operating module, and a first supporting seat that is disposed on said supporting module, said first rotating module rotating relative to said first supporting seat.

9. The stereotactic device as claimed in claim 7, further comprising a second rotating module, said operating module rotating relative to said supporting module along a second rotational direction via said second rotating module, and the first rotational direction being substantially perpendicular to the second rotational direction.

10. The stereotactic device as claimed in claim 9, wherein the second rotating module includes a second supporting seat that is disposed on said supporting module, and a pivot axle that is disposed on said second supporting seat, said first rotating module being pivotably connected to said pivot axle to rotate relative to said second rotating module.

11. The stereotactic device as claimed in claim 1, further comprising a second rotating module, said operating module rotating relative to said supporting module in a second rotational direction via said second rotating module.

12. The stereotactic device as claimed in claim 1, further comprising a rotating module that includes a first connecting part disposed on said supporting module, and a second connecting part disposed on said operating module and rotating relative to said first connecting part.

* * * * *